(12) United States Patent
Wool

(10) Patent No.: US 10,278,792 B2
(45) Date of Patent: May 7, 2019

(54) CRIMPABLE RETRACTION LOOP

(71) Applicant: Suzanne Wool, Sinking Spring, PA (US)

(72) Inventor: Suzanne Wool, Sinking Spring, PA (US)

( * ) Notice: Subject to any disclaimer, the term of this patent is extended or adjusted under 35 U.S.C. 154(b) by 0 days.

(21) Appl. No.: 15/909,711

(22) Filed: Mar. 1, 2018

(65) Prior Publication Data
US 2018/0185120 A1 Jul. 5, 2018

Related U.S. Application Data

(63) Continuation-in-part of application No. PCT/US2016/055424, filed on Sep. 12, 2016.

(60) Provisional application No. 62/262,236, filed on Dec. 2, 2015.

(51) Int. Cl.
A61C 3/00 (2006.01)
A61C 7/02 (2006.01)
A61C 7/12 (2006.01)
A61C 7/14 (2006.01)
A61C 7/22 (2006.01)

(52) U.S. Cl.
CPC ............... *A61C 7/026* (2013.01); *A61C 7/12* (2013.01); *A61C 7/14* (2013.01); *A61C 7/22* (2013.01)

(58) Field of Classification Search
CPC .... A61C 7/20; A61C 7/22; A61C 7/10; A61C 7/026; A61C 7/12; A61C 7/14
USPC .......................................................... 433/22
See application file for complete search history.

(56) References Cited

U.S. PATENT DOCUMENTS

| 3,893,241 | A | * | 7/1975 | Moriarty | A61C 7/12 433/22 |
| 4,571,179 | A | * | 2/1986 | Balenseifen | A61C 7/00 433/20 |
| 5,718,576 | A | * | 2/1998 | Schnaitter | A61C 7/36 433/19 |
| 5,816,800 | A | * | 10/1998 | Brehm | A61C 7/10 433/7 |
| 5,910,008 | A | * | 6/1999 | Tran | A61C 7/20 433/20 |
| 6,341,956 | B1 | * | 1/2002 | Liou | A61C 7/12 433/17 |
| 2002/0098460 | A1 | * | 7/2002 | Farzin-Nia | A61C 7/14 433/13 |

(Continued)

*Primary Examiner* — Nicholas D Lucchesi

(57) ABSTRACT

An accessory allows for straight archwires to be converted to looped archwires. The accessory has an archwire receiving channel which is defined between a first elongated coupling member and a second elongated coupling member. The archwire receiving channel is used for crimping the accessory to an existing archwire. An elastically deformable bridge, connected between the first elongated coupling member and the second elongated coupling member, imparts retraction or protraction once activated. The elastically deformable bridge is formed from one or more segments. Curved segments and linear segments are possible, which can be combined to form various shapes, for example omega loops and mushroom shapes. The first coupling member and the second coupling member have an angled lower portion and upper portion to facilitate engagement with existing archwires. Anchoring notches can also be used in conjunction with elastic bands for enhanced orthodontic corrections.

13 Claims, 11 Drawing Sheets

(56) References Cited

U.S. PATENT DOCUMENTS

| | | | | |
|---|---|---|---|---|
| 2006/0068354 A1* | 3/2006 | Jeckel | ...................... | A61C 7/00 433/21 |
| 2008/0057457 A1* | 3/2008 | Inman | ...................... | A61C 7/20 433/6 |
| 2009/0017412 A1* | 1/2009 | Wool | ...................... | A61C 7/00 433/22 |
| 2009/0047614 A1* | 2/2009 | Fathianathan | ........... | A61C 7/08 433/6 |
| 2010/0297570 A1* | 11/2010 | Bednaz | ................... | A61C 7/00 433/22 |
| 2012/0208144 A1* | 8/2012 | Chiaramonte | ........... | A61C 7/20 433/20 |
| 2013/0149659 A1* | 6/2013 | Garnett | ................... | A61C 7/22 433/20 |
| 2014/0170586 A1* | 6/2014 | Cantarella | ................ | A61C 7/12 433/22 |
| 2014/0302451 A1* | 10/2014 | Berry | ...................... | A61C 7/10 433/18 |
| 2015/0157421 A1* | 6/2015 | Martz | ...................... | A61C 7/08 433/6 |
| 2016/0184067 A1* | 6/2016 | Parker | ..................... | A61C 7/12 433/18 |
| 2017/0156823 A1* | 6/2017 | Roein Peikar | ......... | A61C 7/145 |
| 2017/0196660 A1* | 7/2017 | Lee | .......................... | A61C 7/20 |
| 2018/0221113 A1* | 8/2018 | Tong | ........................ | A61C 7/20 |

* cited by examiner

CRIMPABLE RETRACTION LOOP

The current application is a continuation-in-part (CIP) application of the Patent Cooperation Treaty (PCT) application PCT/US2016/055424 filed on Sep. 16, 2016. The PCT application PCT/US2016/055424 claims priority to U.S. provisional application Ser. No. 62/212,908 filed on Sep. 1, 2015 and claims priority to U.S. provisional application Ser. No. 62/262,236 filed on Dec. 2, 2015.

FIELD OF THE INVENTION

The present invention relates generally to an orthodontic accessory which can be retrofitted to existing archwires via crimping for conversion from straight archwires to looped archwires.

BACKGROUND OF THE INVENTION

Orthodontics is a specialized field of dentistry, dealing primarily with the correction of teeth and jaw position. To adjust a patient's teeth and/or bite, orthodontists attach or insert various devices into their mouth, such as orthodontic brackets (braces), spacers, and retainers. Brackets are bonded directly onto two or more adjacent teeth, being connected by an archwire. The archwire is a thin metal line which applies directional pressure to the teeth in order to produce movement and tooth alignment. Problems exist, as bracket-actuated tooth movement is a slow process, due to the fact that many archwires do not provide enough force.

It is therefore an objective of the present invention to introduce a crimpable retraction loop. The present invention is universally adaptable; it can serve as an orthodontic recoil device which is compatible with any archwire. The present invention is used for creating anterior and posterior closing of spaces, also being able to be used as torquing accessory. The present invention can be used horizontally or vertically on any arch form alloy and is easily used by technicians. The present invention will close spaces, make room for eruptions, accomplish closing diastemas, and an accessory for torquing or tipping.

An orthodontist can position the present invention in any desired orientation. That is, the present invention may be placed vertically, vertically with tipping (i.e. at an angle for desired torque), or horizontally for closing diatoms aesthetically. An orthodontist (or assistant technician) can pull on the present invention to create a desire amount of tooth movement. Once the orthodontist pulls with the desired force, the present invention is crimped in place. It is possible to use orthodontic bands with the present invention, which help pull the teeth to the desired spacing.

A number of variations are possible with the present invention. The present invention can be changed in size to better fit individual patients. For example, the present invention may be produced in a range of millimeter widths to accommodate a different patients' upper arches and lower arches (i.e. the arch shaped arrangement top row and bottom row of teeth). Resultantly, the present invention can be positioned anywhere along the arched wire to close spaces. An additional use for the present invention is to spread the crimping surface and to open the legs of the loop, crimping mesially and distally of a bracket to be used in tipping or torquing.

Another possibility is to use multiple embodiments to increase the amount of force available for repositioning teeth. The present invention can be used on anterior and posterior adjustments, and can be made from a variety of materials, such as stainless steel or beta titanium.

The present invention is advantageous compared to existing orthodontic solutions as movement is initiated directly by the present invention, rather than through the typical accessories which are bonded to brackets or individual teeth. The present invention enables both retraction and protraction and can be installed chairside by an orthodontic assistant. It is additionally compatible with existing ligated archwires and, once activated, results in faster tooth movement as compared to traditional orthodontic solutions.

DETAIL DESCRIPTIONS OF THE INVENTION

All illustrations of the drawings are for the purpose of describing selected versions of the present invention and are not intended to limit the scope of the present invention.

Figure 1:
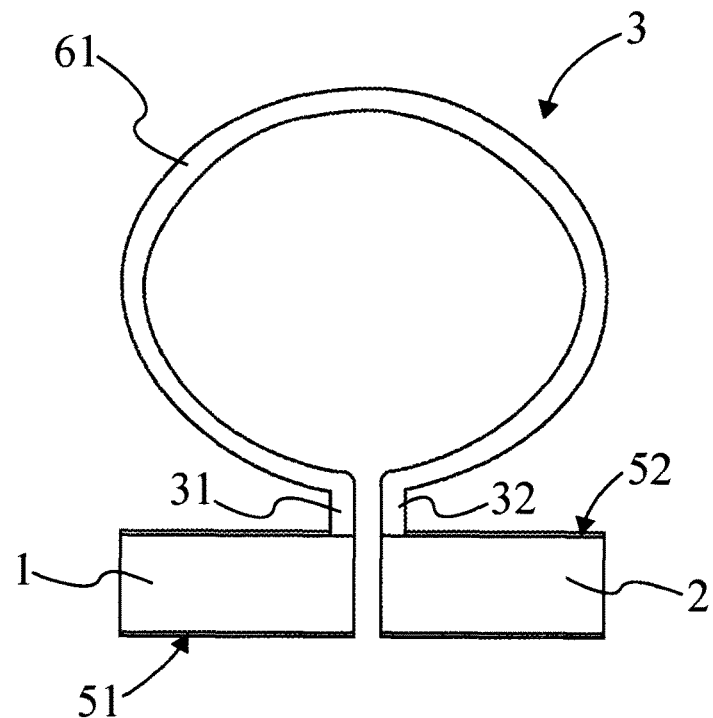
FIG. 1 is a front elevational view showing a first preferred loop shape of the present invention.
Figure 2:
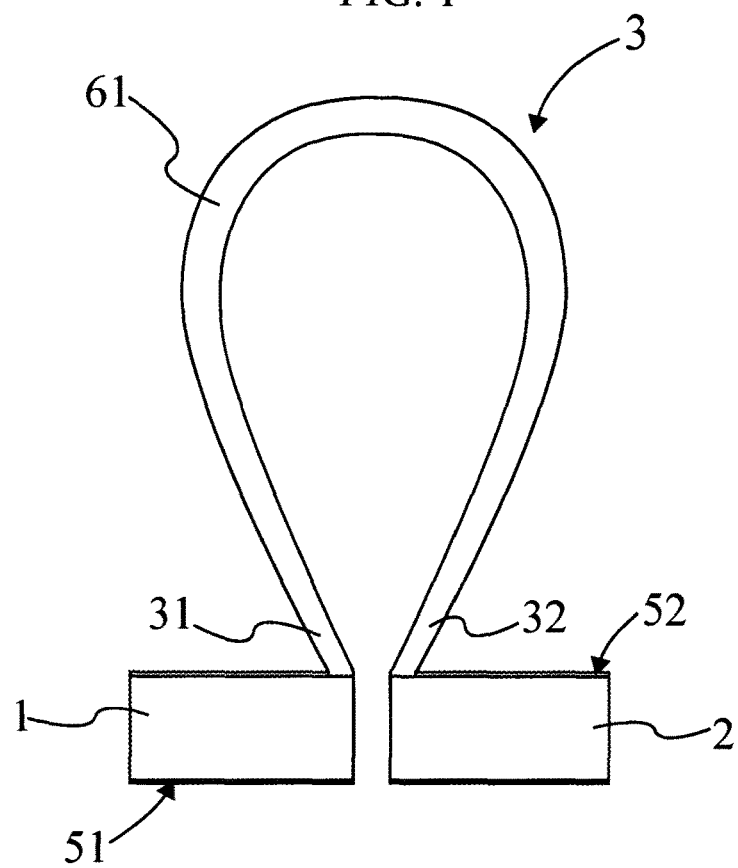
FIG. 2 is a front elevational view showing a second preferred loop shape of the present invention.

The present invention is a retraction loop provided for orthodontic applications. The present invention is compatible with existing dental archwire thanks to a crimpable construction. In support of this, the present invention comprises a first elongated coupling member 1, a second elongated coupling member 2, an elastically deformable bridge 3, and an archwire-receiving channel 4. The first elongated coupling member 1 and the second elongated coupling member 2 serve as interfaces between the present invention and an existing archwire; said elongated coupling members are designed such that they can be secured to an archwire through crimping. The elastically deformable bridge 3 serves as a "recoil device", i.e. it creates tension that helps to realign teeth into a desired position. The archwire-receiving channel 4 engages with an archwire prior to crimping, helping to secure the present invention to an existing archwire. The present invention, including several potential embodiments, is illustrated via FIG. 1-FIG. 12. FIG. 1 and FIG. 2 show the preferred loop shapes for the present invention, while the remaining figures show potential loop shapes for alternative embodiments.

Further defining these components introduced above, the elastically deformable bridge 3 comprises a first free end 31 and a second free end 31. The first free end 31 and the second free end 32 serve as connection points between the elastically deformable bridge 3 and each of the elongated coupling members. On one end of the elastically deformable bridge 3, the first free end 31 is adjacently connected to the first elongated coupling member 1. At the other end of the elastically deformable bridge 3, the second free end 32 is adjacently connected to the second elongated coupling member 2. Effectively, the elastically deformable bridge 3 is bounded on either end by the elongated coupling members. This allows for the elastically deformable bridge 3 to "push" or "pull" on the elongated coupling members and crimped archwire in order to adjust the alignment and position of teeth as deemed necessary by an orthodontist.

Potentially, to connect the elastically deformable bridge 3 to the first elongated coupling member 1 and the second elongated coupling member 2, a coiled extension can be provided for each end of the elastically deformable bridge 3. For example, with an omega loop version, the ends can be spun into circles, which in turn can squeeze right onto the elongated coupling members and subsequently be crimped to an existing archwire.

The first elongated coupling member 1 and the second elongated member 2 each comprise a concave crimping surface 5. The concave crimping surface 5 provides sufficient room to receive an archwire before being crimped. Thus, the concave crimping surface 5 of both elongated members delineates the archwire-receiving channel 4. Certain dimensions for the first elongated coupling member 1, the second elongated coupling member 2, and concave crimping surface 5 are preferable for optimal engagement between the archwire-receiving channel 4 and an archwire; these dimensions will be defined in a later section.

Several configurations are possible for the elastically deformable bridge 3, within the constraints of the elastically deformable bridge 3 being connected between the first elongated coupling member 1 and the second elongated coupling member 2. These potential configurations can be used to alter the elastic properties (for example, the effective "spring constant") of the elastically deformable bridge 3, allowing the present invention to be adjusted to the specific needs of individual patients.

Figure 3:
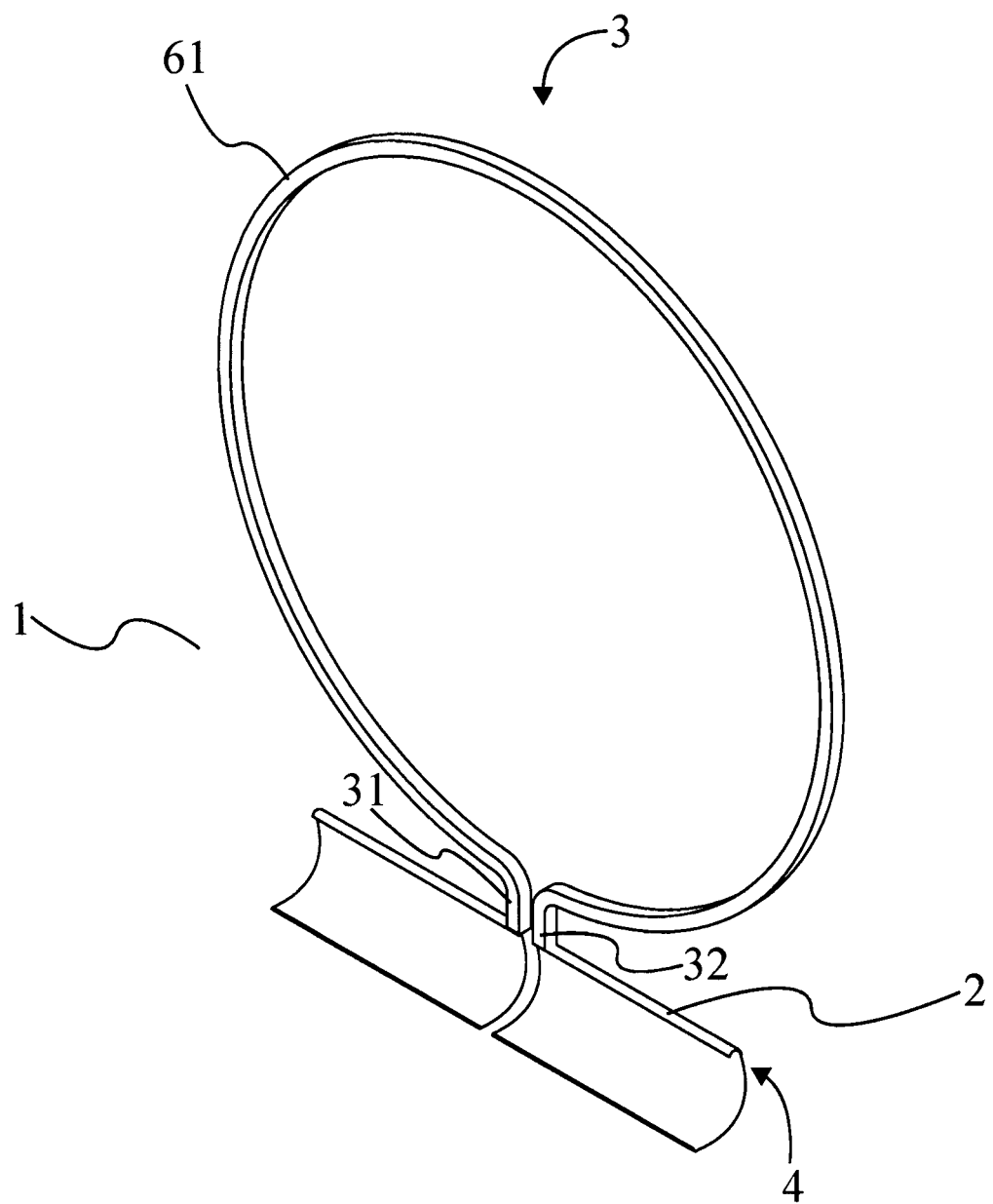
FIG. 3 is a perspective view showing an elastically deformable bridge of the present invention with a potential omega-loop shape.
Figure 4:
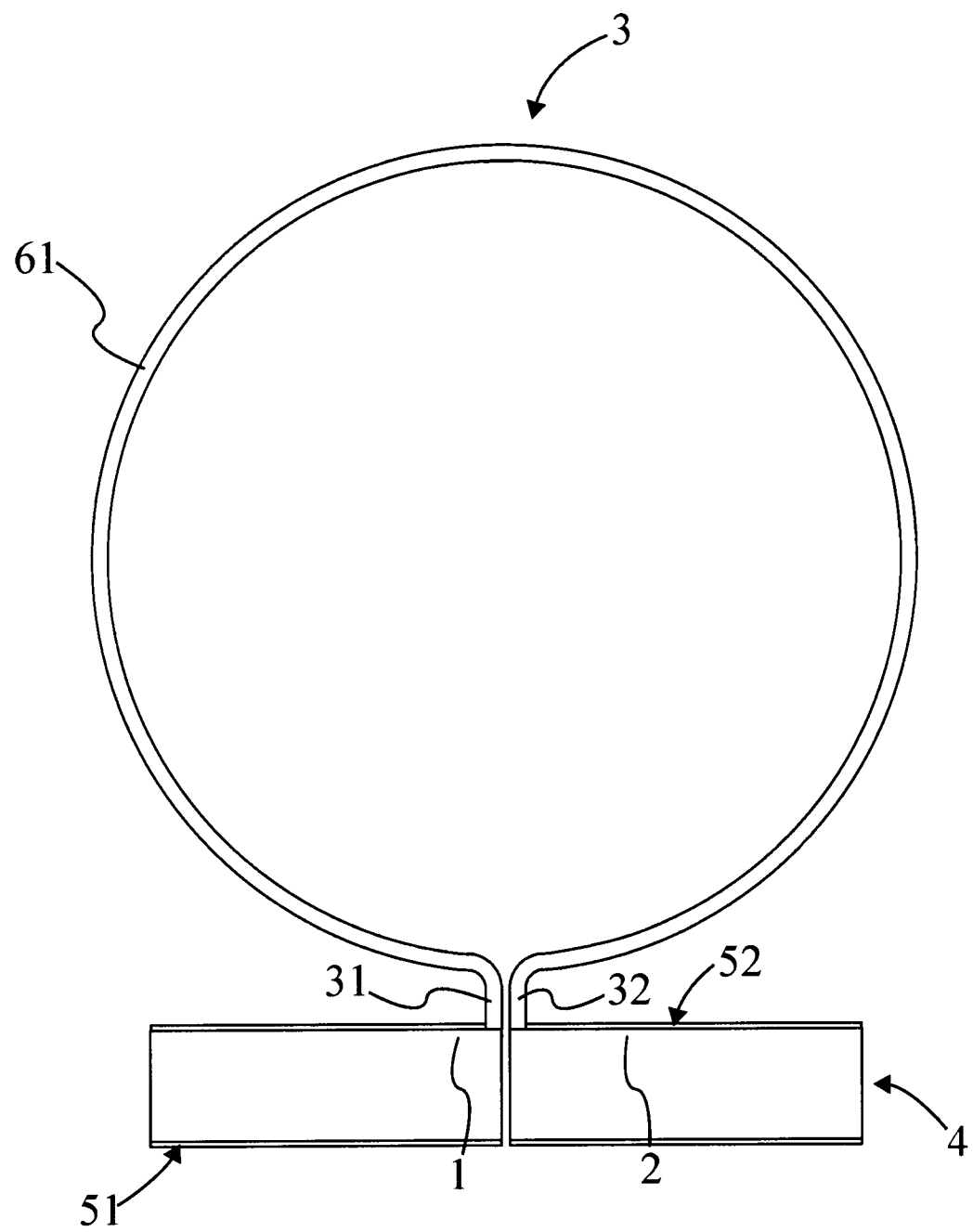
FIG. 4 is a front elevational view showing the omega-loop shape embodiment of the present invention.

In one embodiment, the elastically deformable bridge 3 comprises an at least one curved segment 6. This at least one curved segment 6 is connected between the first free end 31 of the elastically deformable bridge 3 and the second free end 32 of the elastically deformable bridge 3. The specific number of curved segments 6, as well the manner in which they are connected, is not limited by the present invention. For example, in one implementation of a curved segment 6 embodiment, the at least one curved segment 6 is an arc segment 61. This single arc segment 61 results in an (omega) loop-shaped elastically deformable bridge 3, as shown in FIG. 3 and FIG. 4.

Figure 5:
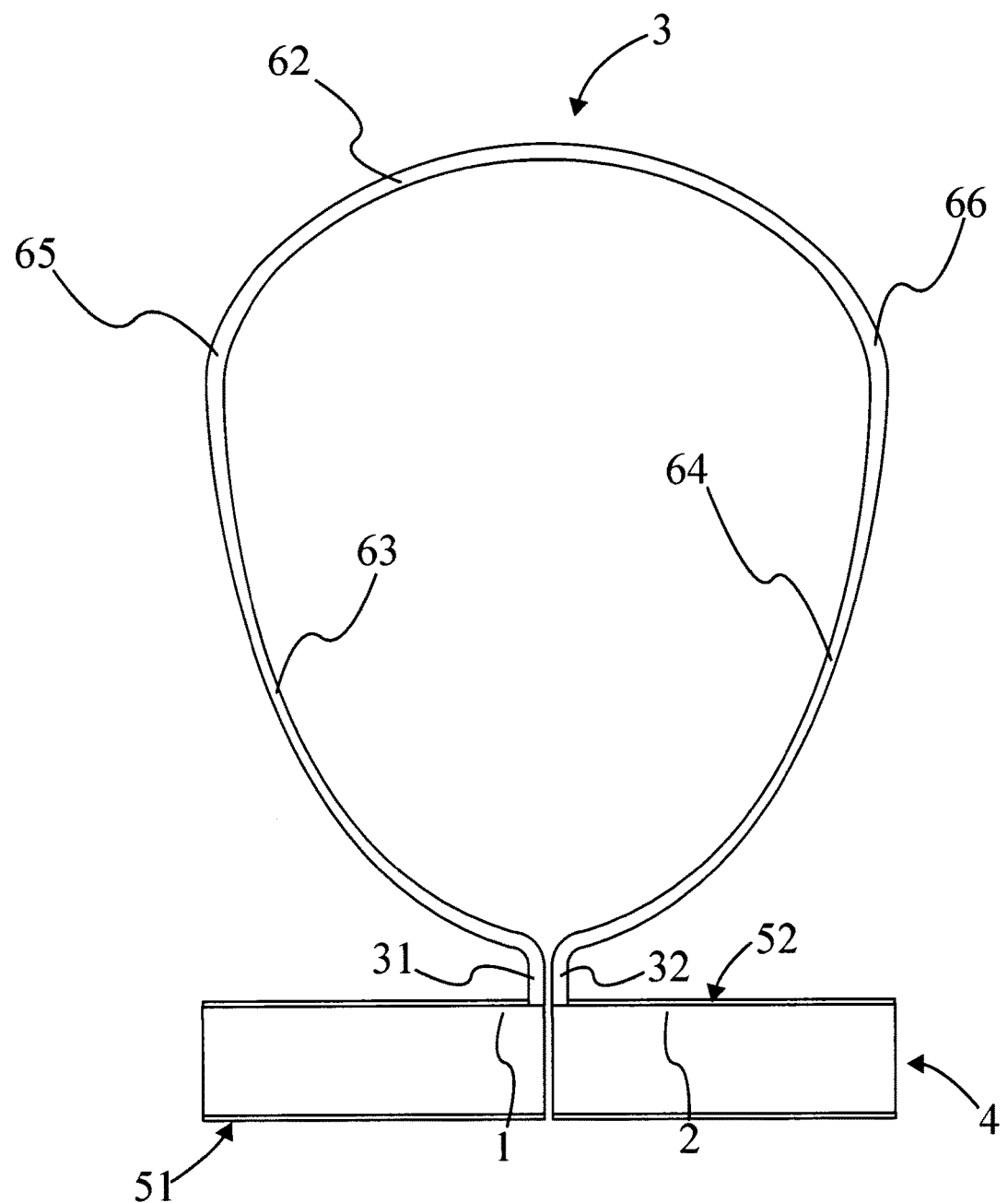
FIG. 5 is a front elevational view showing the elastically deformable bridge of the present invention with a teardrop shape.

In another implementation of a curved segment 6 embodiment, the at least one curved segment 6 comprises a primary arc segment 62, a first connecting arc segment 63, and a secondary arc segment 64. The primary arc segment 62 comprises a first end 65 and a second end 66. The first connecting arc segment 63 is connected between the first end 65 of the primary arc segment 62 and the first free end 31 of the elastically deformable bridge 3. The second connecting arc segment 64 is connected between the second end 66 of the primary arc segment 62 and the second free end 32 of the elastically deformable bridge 3. The connection between the primary arc segment 62 and each of the secondary arc segments is illustrated as maintaining a concave form, resulting in a teardrop-shaped elastically deformable bridge 3. However, the connections between the primary arc segment 62 and the secondary arc segments could be inflection points, such that the elastically deformable bridge has both concave and convex segments. FIG. 5 provides an example of such a teardrop-shaped elastically deformable bridge 3.

Alternatively, in one embodiment the elastically deformable bridge comprises at least one linear segment 7. The at least one linear segment 7 is connected between the first free end 31 of the elastically deformable bridge 3 and the second free end 32 of the elastically deformable bridge 3. Two or more linear segments 7 can be sequentially connected to form polygonal shapes. For example, two linear segments 7 could be connected to each other at an angle to form a triangular-shaped elastically deformable bridge 3. Three linear segments 7 could be connected to each other at right angles to form a rectangular-shaped elastically deformable bridge 3. Four and more linear segments 7 are possible as well, each configuration resulting in a different shape for the elastically deformable bridge 3.

Figure 6:
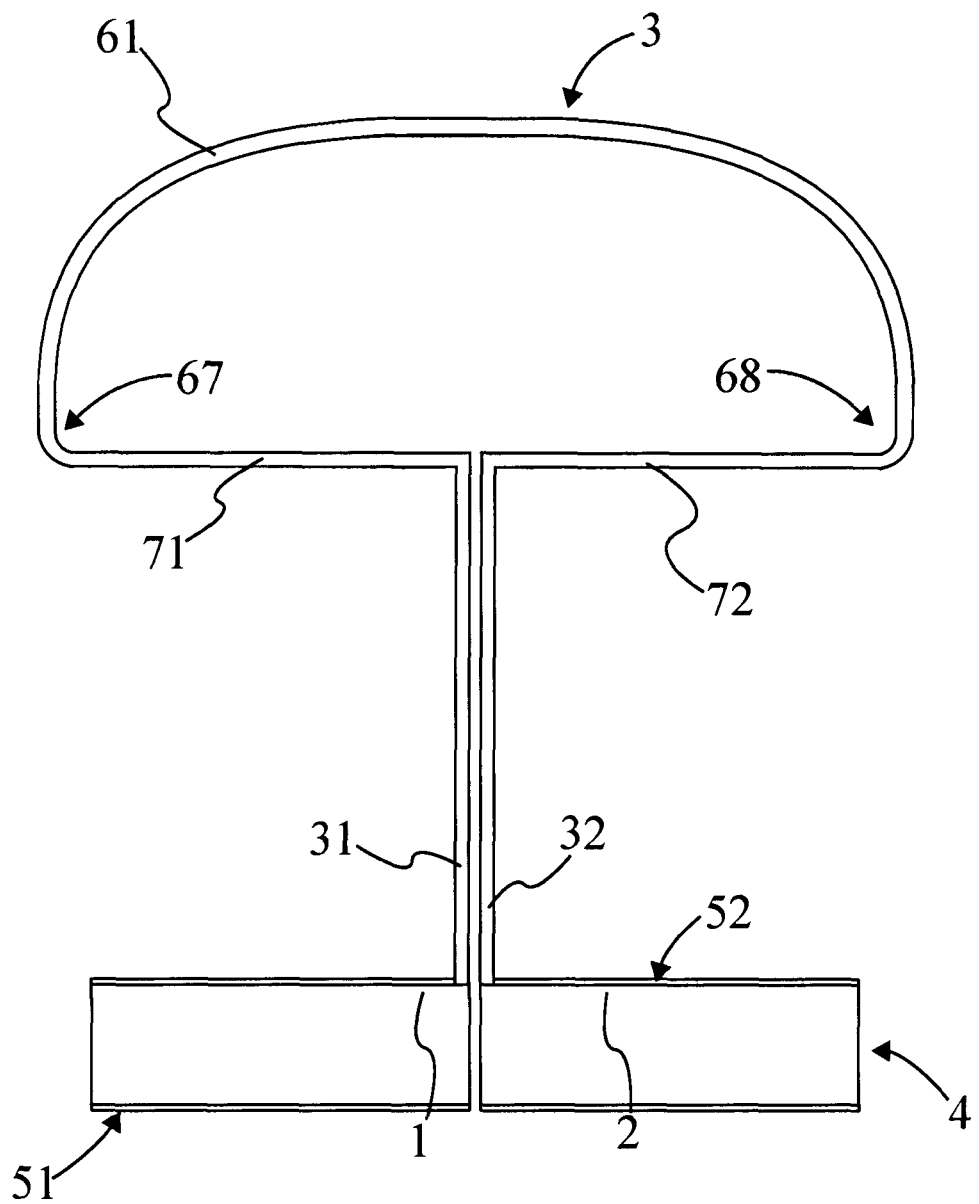
FIG. 6 is a front elevational view showing an elastically deformable bridge of the present invention with a mushroom shape.

In yet another embodiment, the elastically deformable bridge 3 comprise at least one curved segment 6 and at least one linear segment 7. The at least one curved segment 6 and the at least one linear segment 7 are each connected between the first free end 31 and the second free end 32 of the elastically deformable bridge 3. The use of both curved segments 6 and linear segments 7 allows for a greater variety of shapes for the elastically deformable bridge 3. For example, in one implementation the at least one curved segment 6 comprises an arc segment 61 while the at least one linear segment 7 comprises a first linear segment 71 and a second linear segment 72. The arc segment 61 itself comprises a first end 67 and a second end 68. The first linear segment 71 is connected between the first end 67 of the arc segment 61 and the first free end 31 of the elastically deformable bridge 3. Likewise, the second linear segment 72 is connected between the second end 68 of the arc segment 61 and the second free end 32 of the elastically deformable bridge 3. This results in a mushroom-shaped elastically deformable bridge 3 with filleted (curved) edges rather than hard corners. An example of this shape for the elastically deformable bridge 3 is shown in FIG. 6.

For another example implementation of an embodiment with both curved segments 6 and linear segments 7, the at least one curved segment 6 comprises an arc segment 61 while the at least one linear segment 7 comprises a first linear segment 71, a second linear segment 72, a first arm segment 73, and a second arm segment 74. The first linear segment 71 is adjacently connected to the first free end 31 of the elastically deformable bridge 3 and angularly offset from the first elongated coupling member 1 by 90 degrees; in other words the first linear segment 71 is perpendicular to the first elongated coupling member 1. The second linear segment 72, similarly, is adjacently connected to the second free end 32 of the elastically deformable bridge 3 and oriented at a right angle to the second elongated coupling member 2, such that the second linear segment 72 is perpendicular to the second elongated coupling member 2.

Figure 7:
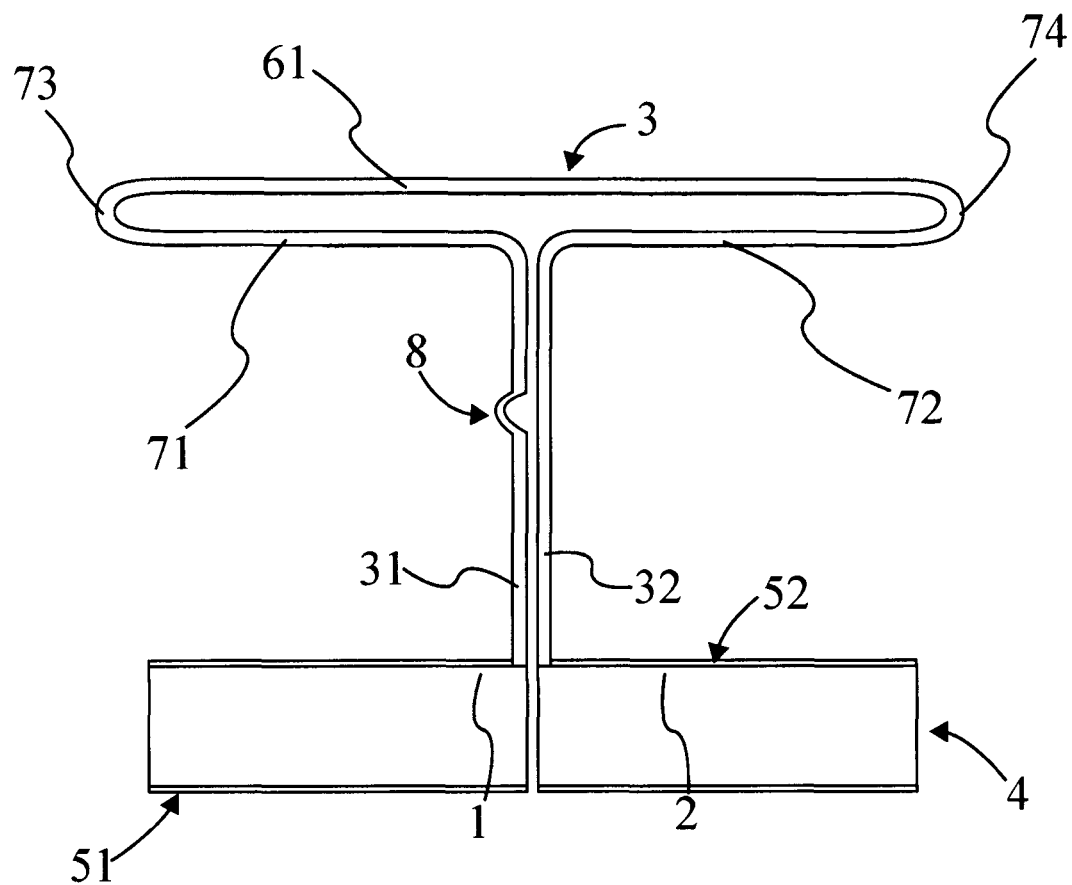
FIG. 7 is a front elevational view showing an elastically deformable bridge of the present invention with a t-shape and an anchoring notch.

The first arm segment 73 and the second arm segment 74 are offset from their corresponding linear segments. The first arm segment 73 is adjacently connected to the first linear segment 71, at an end opposite the first free end 31 of the elastically deformable bridge 3. The second arm segment 74 is adjacently connected to the second linear segment 72, at an end opposite the second free end 32 of the elastically deformable bridge 3. The first arm segment 73 and the second arm segment 74 are also each connected to the arc segment 61, forming the complete elastically deformable bridge 3 in this embodiment. The first arm segment 73 is adjacently connected to the first end 67 of the arc segment 61 and, opposite this first arm segment 73, the second arm segment 74 is adjacently connected to the second end 68 of the arc segment 61. This configuration culminates in a t-shaped elastically deformable bridge 3, as shown in FIG. 7.

Figure 8:
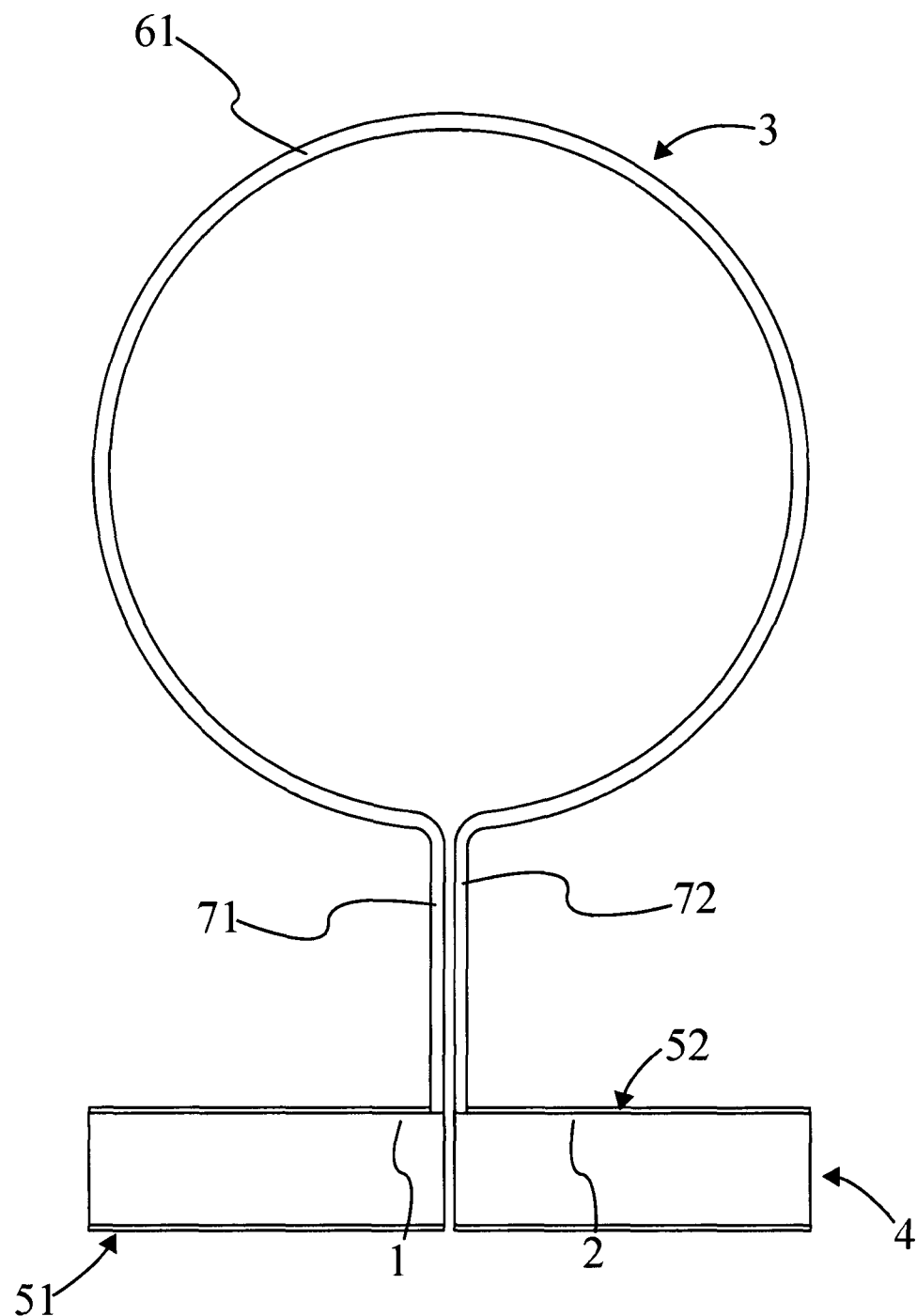
FIG. 8 is a front elevational view showing an elastically deformable bridge of the present invention with a circular loop shape.
Figure 9:
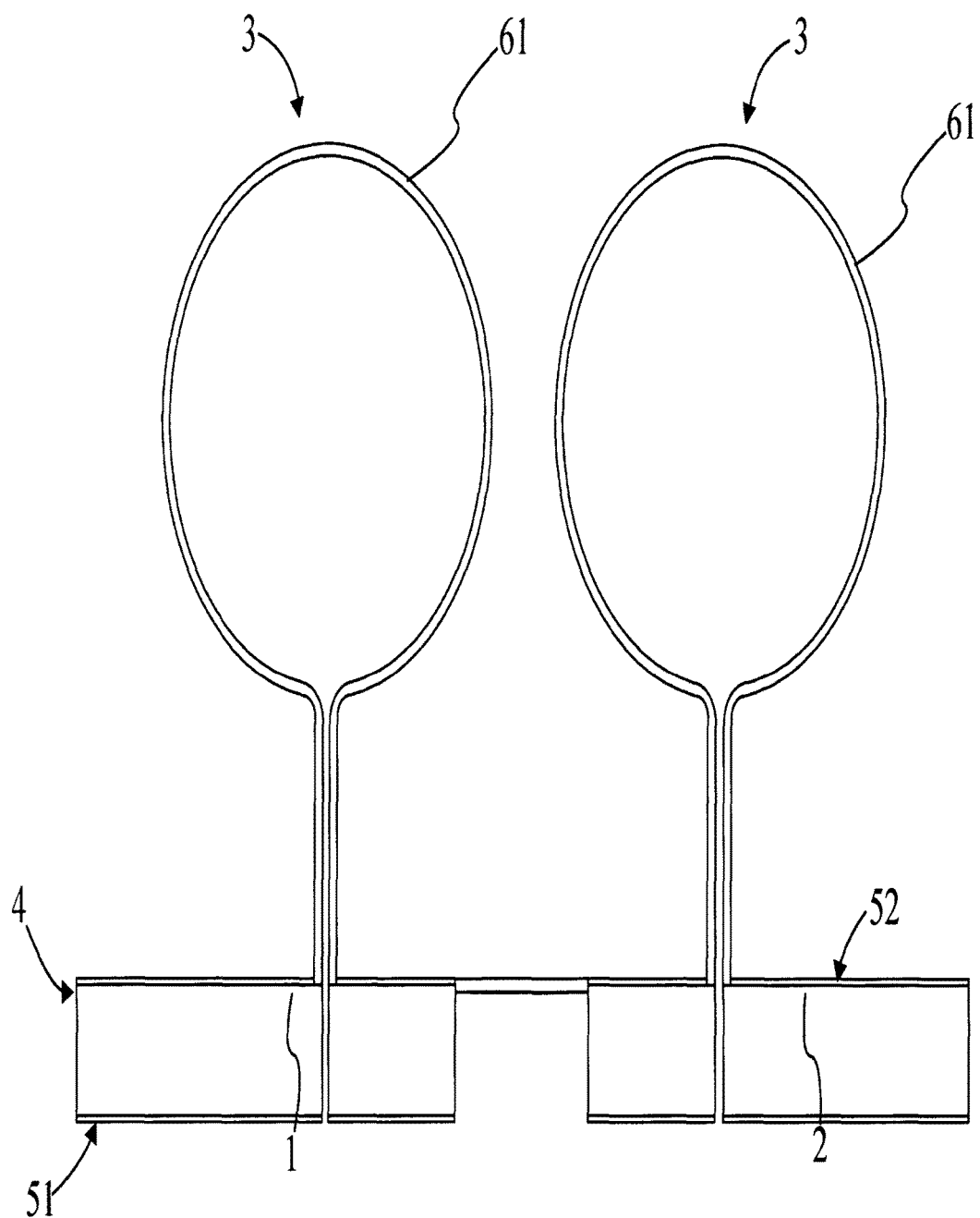
FIG. 9 is a front elevational view a potential embodiment of the present invention with multiple elastically deformable bridges.
Figures 10A, 10B:
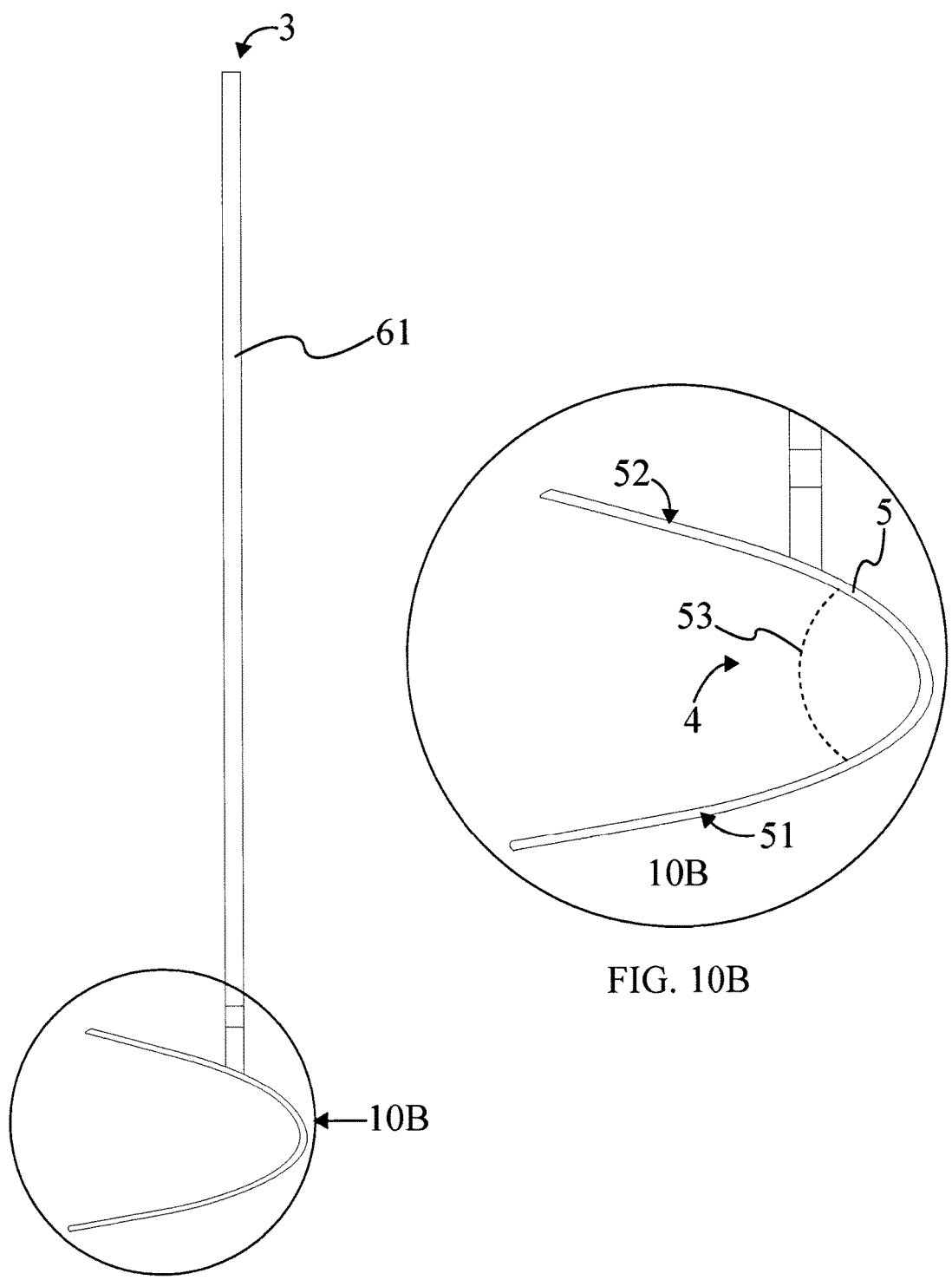
FIG. 10A is a right side view of the present invention.
FIG. 10B is an enhanced right side view of the present invention showing an elongated coupling member prior to crimping.
Figure 11:
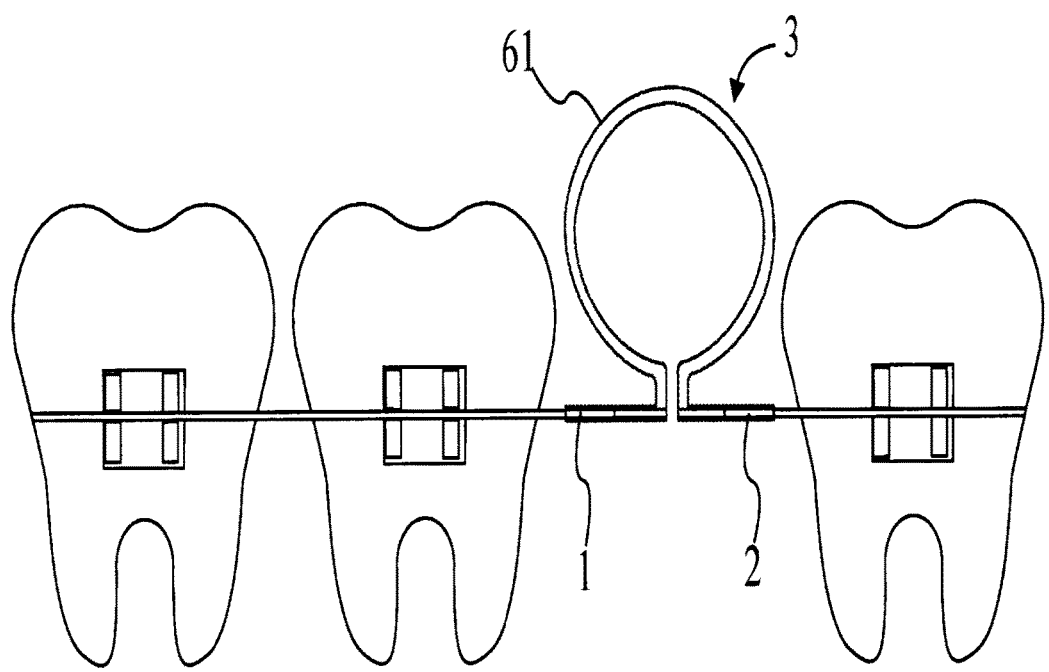
FIG. 11 is a front elevational view showing the activated present invention, connected to an existing archwire.

The above described configurations and resulting shapes for the elastically deformable bridge 3 are just a few potential examples. Ultimately, any variant configurations for the elastically deformable bridge 3 are compatible with the present invention as long as they are capable of exhibiting a pushing or pulling force on the coupled archwire, as necessary to adjust the position of teeth within a patient's mouth. FIG. 8 and FIG. 9 are examples of such, showing a heightened elastically deformable bridge 3 as compared to the omega loop version shown in FIG. 1. Further, multiple elastically deformable bridges 3 could be sequentially connected to each other to increase the corrective capabilities of the present invention; this is because each elastically deformable bridge 3 increases the amount of force available for realigning teeth into a desired position. An example multiple elastically deformable bridges 3 is shown in FIG. 9.

Returning to the archwire-receiving channel 4, which allows for the present invention to be retrofitted to an existing archwire, the concave crimping surface 5 comprises a lower portion 51 and an upper portion 52. These two portions are offset from each other at an acute angle 53, providing sufficient room for receiving an archwire. Once an archwire is placed in the archwire-receiving region 4 and the two portions are crimped together, the archwire is effectively secured between the lower portion 51 and the upper portion 52. Resultantly, the present invention is joined to an existing archwire.

Preferably, the lower portion 51 and the upper portion 52 are offset from each other at an acute angle 53. The acute angle 53 provides sufficient space for insertion of the archwire while minimizing the profile of the present invention. This makes it easier for a dental professional to maneuver and otherwise manipulate the present invention for connection to an existing archwire. While the acute angle is not restricted by the present invention, an optimal range has been found; thus, it is preferable that the acute angle 53 is greater than or equal to 20 degrees and less than or equal to 25 degrees. The elongated coupling members are more clearly illustrated in FIG. 10A and FIG. 10B.

Figure 12:
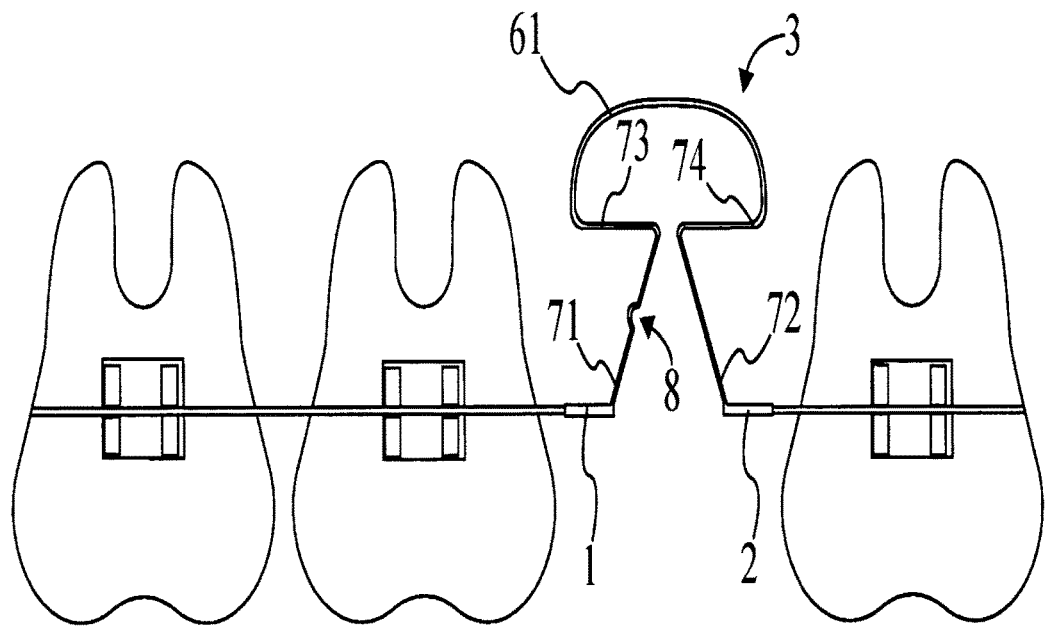
FIG. 12 is a front elevational view showing the present invention in use with an orthodontic elastic band.
Figure 12:
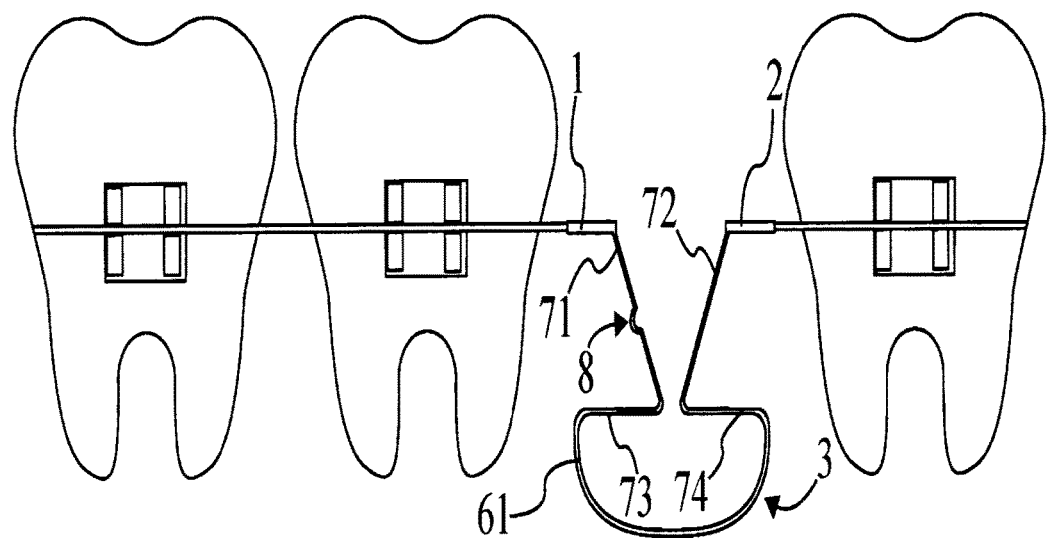

Beyond the components and configurations described above, additions remain possible within the scope of the present invention. For example, the present invention can comprise an anchoring notch 8. The anchoring notch 8 is integrated into the elastically deformable bridge 3, forming a coupling point for orthodontic accessories such as elastic bands 9 (used to create additional tension that further helps with adjusting tooth positioning). The anchoring notch 8 allows for adjacent elastically deformable bridges 3 to pull adjacent teeth together, when joined to each other by an elastic band 9. The adjacent teeth can be adjacent across the superior teeth and the inferior teeth (i.e. top row and bottom row) or along the superior teeth or inferior teeth. Multiple anchoring notches 8 can be provided on an individual elastically deformable bridge 3 to afford a dental specialist some flexibility when choosing the specific position at which to couple an elastic band to the elastically deformable bridge 3. Potentially, anchoring notches 8 could even be integrated into the elongated coupling members. And embodiment showing an anchoring notch 8 is depicted in FIG. 9 and FIG. 12.

The present invention is intended to be easy to install with existing archwires, such that an orthodontic assistant is able to place the present invention in a person's mouth without supervision. This is beneficial as it frees up time from an orthodontist's busy schedule. Installation of the present invention entails the following steps. First, the first elongated coupling member 1 and the second elongated coupling member 2 are aligned with an existing archwire. The two coupling members are then moved towards the archwire, such that the archwire moves into the archwire-receiving channel 4, the latter being formed between the bottom portion 51 and the top portion 52 of the concave crimping surface 5.

Once the two coupling members have been appropriately positioned with respect to the existing archwire, they are crimped close, securing the present invention to aforementioned archwire. The archwire, now secured within the archwire-receiving channel 4, can then be snipped to activate the present invention; once the intermediate archwire (in the area between the first elongated coupling member 1 and the second elongated coupling member 2) is snipped the present invention is able to exert a force on each end of the now disjointed archwire. Multiple copies of the present invention can be utilized if desired, for example distributed across a patient's teeth to more effectively impact a larger area. Further, elastic bands 9 may be coupled with adjacent elastically deformable bridges 3 (and their corresponding anchoring notches 8) in order to increase the force between two segments of archwire. The present invention is compatible with both traditional style braces (e.g. "standard bracket systems", in addition to alternative braces (e.g. with "self-ligating brackets") or ultimately any sort of dental system that uses an archwire or similar component. The use of an elastic band 9, along with anchoring notches 8, is illustrated via FIG. 12.

While the dimensions of the present invention are not restricted, certain dimensions are utilized in a preferred embodiment. In this preferred embodiment, the first elongated coupling member and the second elongated coupling member are each 2 mm in length, creating a total length of 4 mm. The height of the elongated coupling members, prior to crimping (measured from the lower portion to the upper portion) is 1.3 mm.

The height of the elastically deformable bridge varies according to the shape. For example, a basic "omega" loop shape would have a 3 mm height. Other shapes, including mushroom, teardrop, "T", mountain, and "P", would have heights of 4 mm. These heights are in addition to the height of the elongated coupling members, and measured after crimping (such that the elastically deformable bridges are vertical with respect to the elongated coupling members). Generally, regardless of the specific shape of the elastically deformable bridge, its height will range from a minimum of 3 mm to a maximum of 4 mm. Further, the depth of each elongated coupling member, including the bottom portion and the top portion, is preferably set to be 1 mm.

Although the invention has been explained in relation to its preferred embodiment, it is to be understood that many other possible modifications and variations can be made without departing from the spirit and scope of the invention as hereinafter claimed.

What is claimed is:

1. A crimpable retraction loop apparatus comprising:
a first elongated coupling member;
a second elongated coupling member;
an elastically deformable bridge;
the elastically deformable bridge comprising a first free end and a second free end;
the first free end and the second free end being oppositely located to each other;
the first elongated coupling member comprising a first elongated opening, a first concave crimping surface and a first archwire-receiving channel;
the second elongated coupling member comprising a second elongated opening, a second concave crimping surface and a second archwire-receiving channel;
the first free end being connected to the first elongated coupling member;
the second free end being connected to the second elongated coupling member;
the first elongated coupling member being connected to the second elongated coupling member by the elastically deformable bridge;
the first archwire-receiving channel being delineated by the first elongated opening and the first concave crimping surface;
the second archwire-receiving channel being delineated by the second elongated opening and the second concave crimping surface;
the first elongated coupling member and the second elongated coupling member being substantially aligned with each other;
the first concave crimping surface comprising a first lower portion and a first upper portion;
the first lower portion and the first upper portion being offset from each other;
the first lower portion and the first upper portion being separate from each other via the first elongated opening;
the second concave crimping surface comprising a second lower portion and a second upper portion;
the second lower portion and the second upper portion being offset from each other; and
the second lower portion and the second upper portion being separate from each other via the second elongated opening.

2. The crimpable retraction loop apparatus as claimed in claim 1 comprising:
the elastically deformable bridge comprising at least one curved segment; and
the at least one curved segment being formed in between the first free end and the second free end.

3. The crimpable retraction loop apparatus as claimed in claim 2 comprising:
the at least one curved segment being an arc segment; and
the elastically deformable bridge being of loop-shaped.

4. The crimpable retraction loop apparatus as claimed in claim 2 comprising:
the at least one curved segment comprising a primary arc segment, a first connecting arc segment and a second connecting arc segment;
the primary arc segment being formed in between the first connecting arc segment and the second connecting arc segment;
the primary arc segment comprising a first end and a second end;
the first connecting arc segment being formed in between the first end and the first free end; and
the second connecting arc segment being formed in between the second end and the second free end.

5. The crimpable retraction loop apparatus as claimed in claim 1 comprising:
the elastically deformable bridge comprising at least one linear segment; and
the at least one linear segment being formed in between the first free end of the elastically deformable bridge and the second free end.

6. The crimpable retraction loop apparatus as claimed in claim 1 comprising:
the elastically deformable bridge comprising at least one curved segment and at least one linear segment;
the at least one curved segment being formed in between the first free end and the second free end; and
the at least one linear segment being formed in between the first free end and the second free end.

7. The crimpable retraction loop apparatus as claimed in claim 6 comprising:
the at least one curved segment comprising an arc segment;
the arc segment comprising a first end and a second end;
the at least one linear segment comprising a first linear segment and a second linear segment;
the first linear segment being formed in between the first end and the first free end; and
the second linear segment being formed in between the second end and the second free end.

8. The crimpable retraction loop apparatus as claimed in claim 6 comprising:
the at least one curved segment comprising an arc segment;
the at least one linear segment comprising a first linear segment, a second linear segment, a first arm segment and a second arm segment;
the arc segment comprising a first end and a second end;
the first linear segment being formed in between the first free end and the first arm segment;
the first linear segment being perpendicularly located to the first elongated coupling member;
the second linear segment being formed in between the second free end and the second arm segment;
the second linear segment being perpendicularly located to the second elongated coupling member;
the first arm segment being formed in between the first end and the first linear segment; and
the second arm segment being formed in between the second end and the second linear segment.

9. The crimpable retraction loop apparatus as claimed in claim 1 comprising:
the first upper portion being offset from the first lower portion at a first acute angle.

10. The crimpable retraction loop apparatus as claimed in claim 9, wherein the first acute angle is from 20 degrees to 25 degrees.

11. The crimpable retraction loop apparatus as claimed in claim 1 comprising:
an anchoring notch;
the anchoring notch being integrated into the elastically deformable bridge;

an elastic band; and the elastic band being coupled with the anchoring notch.

12. The crimpable retraction loop apparatus as claimed in claim 1 comprising:

the second upper portion being offset from the second lower portion at a second acute angle.

13. The crimpable retraction loop apparatus as claimed in claim 12, wherein the second acute angle is from 20 degrees to 25 degrees.

* * * * *